(12) United States Patent
Hirata

(10) Patent No.: US 9,606,090 B2
(45) Date of Patent: Mar. 28, 2017

(54) ANALYSIS DEVICE WITH SIMULTANEOUS INDUCTION AND LASER HEATING AND ANALYSIS METHOD THEREWITH

(71) Applicant: HORIBA, Ltd., Kyoto-shi, Kyoto (JP)

(72) Inventor: Yasushi Hirata, Kyoto (JP)

(73) Assignee: HORIBA, LTD., Kyoto-Shi, Kyoto (JP)

( * ) Notice: Subject to any disclaimer, the term of this patent is extended or adjusted under 35 U.S.C. 154(b) by 0 days.

(21) Appl. No.: 15/022,334

(22) PCT Filed: Sep. 10, 2014

(86) PCT No.: PCT/JP2014/073903
§ 371 (c)(1),
(2) Date: Mar. 16, 2016

(87) PCT Pub. No.: WO2015/045869
PCT Pub. Date: Apr. 2, 2015

(65) Prior Publication Data
US 2016/0231298 A1 Aug. 11, 2016

(30) Foreign Application Priority Data

Sep. 25, 2013 (JP) .................................. 2013-198729

(51) Int. Cl.
*G01N 31/12* (2006.01)
*G01N 1/44* (2006.01)
(Continued)

(52) U.S. Cl.
CPC .............. *G01N 31/12* (2013.01); *G01N 1/44* (2013.01); *G01N 33/004* (2013.01); *G01N 33/0042* (2013.01); *H05B 6/24* (2013.01)

(58) Field of Classification Search
CPC ................................. G01N 31/21; G01N 1/44
(Continued)

(56) References Cited

U.S. PATENT DOCUMENTS 3,569,660 A * 3/1971 Houldcroft .......... B23K 26/147
219/121.68
4,305,906 A * 12/1981 Mikasa .................. G01N 30/40
422/62
(Continued)

FOREIGN PATENT DOCUMENTS

CN 1177100 A 3/1998
CN 1390303 A 1/2003
(Continued)

OTHER PUBLICATIONS

International Search Report for International Application No. PCT/JP2014/073903.( Dec. 22, 2014).
(Continued)

*Primary Examiner* — Arlen Soderquist
(74) *Attorney, Agent, or Firm* — Robert P. Michael, Esq.; Carter, DeLuca, Farrell & Schmidt, LLP

(57) ABSTRACT

To efficiently heat and burn a sample without using a combustion aid, an analysis device that heats a sample in a sample accommodation part and analyzes the resulting gas is provided with an induced current generation mechanism for generating an induced current in the sample through electromagnetic induction and a laser irradiation mechanism for irradiating laser light onto the sample and is configured so that the induced current generation mechanism and the laser irradiation mechanism act simultaneously on the sample.

4 Claims, 3 Drawing Sheets

(51) Int. Cl.
*H05B 6/24* (2006.01)
*G01N 33/00* (2006.01)

(58) Field of Classification Search
USPC ............................. 422/78–80; 436/155, 160
See application file for complete search history.

(56) References Cited

U.S. PATENT DOCUMENTS

| | | | | |
|---|---|---|---|---|
| 4,582,686 | A | * | 4/1986 | Tsuji .................... G01N 33/20 422/80 |
| 4,937,424 | A | * | 6/1990 | Yasui .................. H01S 3/08081 219/121.6 |
| 5,155,047 | A | * | 10/1992 | Cioni .................... F23N 5/003 110/347 |
| 5,468,932 | A | * | 11/1995 | Jacob ................. B23K 26/0066 219/121.69 |
| 5,844,149 | A | | 12/1998 | Akiyoshi et al. |
| 6,627,155 | B1 | * | 9/2003 | Uemura ................. G01N 31/12 250/288 |
| 2004/0247483 | A1 | * | 12/2004 | Uemura ................. G01N 31/12 422/80 |
| 2013/0125673 | A1 | * | 5/2013 | Kanipayor ................ B01L 3/04 73/863.11 |
| 2013/0196445 | A1 | | 8/2013 | Kinoshiro et al. |

FOREIGN PATENT DOCUMENTS

| | | |
|---|---|---|
| CN | 101672836 A | 3/2010 |
| JP | 02-264861 A | 10/1990 |
| JP | 03-197835 A | 8/1991 |
| JP | 04-326007 A | 11/1992 |
| JP | 10-203812 A | 8/1998 |
| JP | 2000-28580 A | 1/2000 |
| JP | 2000-266741 A | 9/2000 |
| JP | 2000-321265 A | 11/2000 |
| JP | 2001-305122 A | 10/2001 |
| JP | 2008-008793 A | 1/2008 |
| JP | 2008-151590 A | 7/2008 |
| JP | 2012-47737 A | 3/2012 |
| WO | WO-01/27608 A2 | 4/2001 |
| WO | 2011102137 A1 | 8/2011 |

OTHER PUBLICATIONS

First Office Action issued by the Chinese Patent Office in relation to Chinese Patent Application No. 201480051838.1 dated Dec. 8, 2016 along with English language translation dated Dec. 13, 2016 (12 pages).

* cited by examiner

ANALYSIS DEVICE WITH SIMULTANEOUS INDUCTION AND LASER HEATING AND ANALYSIS METHOD THEREWITH

CROSS REFERENCE TO RELATED APPLICATION

This Application is a 371 of PCT/JP2014/073903 filed on Sep. 10, 2014, which, in turn, claimed the priority of Japanese Patent Application No. JP2013-198729 filed on Sep. 25, 2013, both applications are incorporated herein by reference.

TECHNICAL FIELD

The present invention relates to an analysis device such as an elemental analyzer or the like that analyzes elements such as carbon (C) and sulfur (S) that are contained in a sample of, for example, steel, a non-ferrous metal, or a ceramic or the like, and to an analysis method.

TECHNICAL BACKGROUND

There are some elemental analyzers of this type in which a crucible containing a sample is placed inside a heating furnace. High-frequency AC voltage is then applied to a coil surrounding the crucible so that the sample inside the crucible is heated and combusted by high-frequency induction heating. Elements that are contained in this sample are analyzed from the gas that is thereby generated.

Conventionally, as is shown in Patent document 1, a combustion improver is used in the above-described elemental analyzer in order to accelerate the combustion of the sample.

DOCUMENTS OF THE PRIOR ART

[Patent Documents]
[Patent document 1] Japanese Unexamined Patent Application (JP-A) No. 2000-266741

DISCLOSURE OF THE INVENTION

Problems to be Solved by the Invention

However, if a combustion improver is used, a sizable quantity of dust is generated by the combustion of the combustion improver. Because of this, it is necessary to provide, for example, a dust suction mechanism that suctions dust, and this causes the size of the apparatus to increase. Moreover, even if a dust suction mechanism is provided, if the suction force is inadequate, then dust is left behind in the heating furnace, and if the gas becomes adhered to this dust, then the problem arises that this causes measurement errors to occur.

Furthermore, tungsten, which is a rare metal, is contained in the combustion improver, so that, if a combustion improver is used, the additional problem arises that the running costs incurred by the analysis become expensive.

The present invention was conceived in order to solve the above-described problems, and it is a principal object thereof to make it possible to efficiently heat and combust a sample without using a combustion improver.

Means for Solving the Problem

Namely, the analysis device according to the present invention is an analysis device that heats a sample inside a sample holding portion, and analyzes the gas that is thereby generated, and that is provided with: an induced current generating mechanism that generates by electromagnetic induction an induced current in the sample; and a laser irradiation mechanism that irradiates laser light onto the sample, and the induced current generating mechanism and the laser irradiation mechanism are made to act simultaneously on the sample.

Moreover, the analysis method according to the present invention is an analysis method in which a sample is heated inside a sample holding portion, and the resulting gas that is thereby generated is analyzed, wherein the sample is heated by the induced current generating mechanism, which generates an induced current in the sample by electromagnetic induction, and by the laser irradiation mechanism, which irradiates laser light onto the sample, acting simultaneously on the sample.

By employing this type of analysis device and analysis method, because the induced current generating mechanism and the laser irradiation mechanism are made to act simultaneously to heat the sample, compared with when a sample is heated solely by high-frequency induction heating, as is the case conventionally, it is possible to more efficiently heat the sample and thereby accelerate combustion so that there is no need for a combustion improver to be provided. Because the fact that no combustion improver is used means that no dust resulting from the combustion improver is generated, there is no need for a dust suction mechanism to be provided, and no measurement errors that are caused by gas adhering to the dust are generated.

It is thought that the reason why it is possible to efficiently heat a sample by causing an induced current generating mechanism and a laser irradiation mechanism to act simultaneously in this manner is because the portion of the sample where the laser is irradiated undergoes localized melting, and this melted portion is agitated by the electromagnetic induction, and promotes the melting of the other portions as well. Consequently, the entire sample can be easily melted.

Moreover, it is preferable for the analysis device to be further provided with a flow path forming component in which a supply flow path that supplies oxygen into the interior of the sample holding portion is formed, and for a transmission window that allows to transmit laser light to be formed in the flow path forming component, and for an optical path of the laser light that has been transmitted through the transmission window to be formed inside the supply flow path along with the flow path direction of the supply flow path.

If this type of structure is employed, then because the optical path of the laser light transmitted through the transmission window is formed inside the supply flow path, the existing supply flow path is able to also function as the optical path of the laser light. Accordingly, there is no need for a complicated device structure.

Moreover, because oxygen is supplied from the supply flow path to the interior of the sample holding portion, it is difficult for dust and high-temperature gases and the like that may be generated inside the sample holding portion to enter into the supply flow path, and contamination or breakage of the transmission window can be prevented.

It is also preferable for the supply flow path to have a rectilinear flow path having one end that opens in the direction of the sample, and having the transmission window formed in the other end thereof.

If this type of structure is employed, then because one end of the rectilinear flow path opens towards the sample, laser light that has passed through the transmission window that is formed in the other end can be reliably irradiated onto the sample. In addition, oxygen can be blown towards the sample so that the combustion of the sample is accelerated, and there is even less need for a combustion improver to be provided.

Moreover, because the laser light is irradiated along a rectilinear flow path onto the sample, the laser light that has passed through the transmission window can be guided directly onto the sample through the transmission window without any optical components such as mirrors being used.

Effects of the Invention

According to the present invention having the above-described structure, it is possible to efficiently heat and combust a sample without using a combustion improver.

DESCRIPTION OF THE REFERENCE NUMERALS

Figure 1:
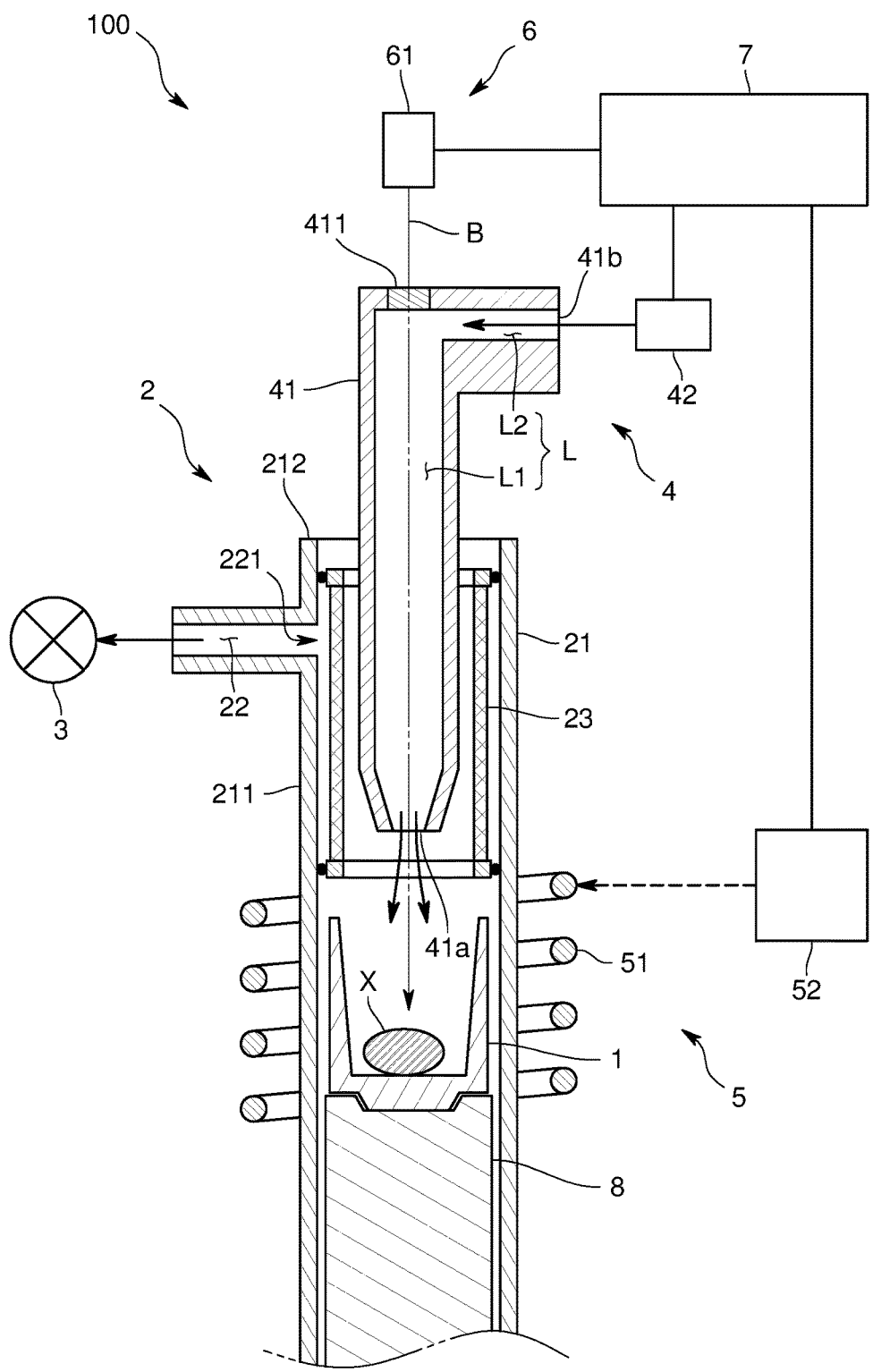
FIG. 1 schematically shows the structure of an elemental analyzer according to the present embodiment.

100 . . . Elemental analyzer
X . . . Sample
1 . . . Crucible
2 . . . Heating furnace
3 . . . Gas analyzer
41 . . . Flow path formation component
411 . . . Transmission window
L . . . Supply flow path
L1 . . . First flow path (Rectilinear flow path)
L2 . . . Second flow path
5 . . . Induction heating mechanism (Induced current generating mechanism)
51 . . . Coil
6 . . . Laser heating mechanism (Laser irradiation mechanism)
61 . . . Laser light source

BEST EMBODIMENTS FOR IMPLEMENTING THE INVENTION

Hereinafter, an embodiment of an elemental analyzer which serves as an example of an analysis device according to the present invention will be described with reference made to the drawings.

An elemental analyzer 100 according to the present embodiment heats and combusts a sample X which is made, for example, from metal or the like, and analyzes elements such as carbon (C) and sulfur (S) and the like that are contained in the sample X from the gas that is thereby generated.

Specifically, as is shown in FIG. 1, this elemental analyzer 100 is equipped with a heating furnace 2 which is a sample housing portion in which a crucible 1 that holds the sample X is placed, a gas analyzer 3 that analyzes the gas generated by the combustion of the sample X, an oxygen supply mechanism 4 that supplies oxygen to the interior of the heating furnace 2, an induced current generating mechanism (induction heating mechanism) 5 that generates an induced current in the sample X inside the crucible 1 via electromagnetic induction so that the sample X is induction heated, a laser irradiation mechanism (laser heating mechanism) 6 that heats the sample X by irradiating laser light onto the sample X, and a control unit 7 that controls operations of the oxygen supply mechanism 4, the induction heating mechanism 5, and the laser heating mechanism 6.

Hereinafter, the respective portions will be described.

The crucible 1 is mounted on a placement stand 8 while internally holding the sample X. In the present embodiment, the crucible 1 is formed, for example, by a magnetic body such as a ceramic material or the like that has a conductive heating element.

Note that the placement stand 8 is constructed such that it can be moved up and down by a cylinder mechanism (not shown) between a heating position where the sample X inside the crucible 1 is heated inside the heating furnace 2, and a removal position where the crucible 1 is mounted on or removed from the placement stand 8.

The heating furnace 2 is constructed such that it heats the sample X that it is holding internally, and then guides the gas that is thereby generated to the gas analyzer 3. The heating furnace 2 is provided with a substantially cylinder-shaped furnace main body 21, a gas outflow path 22 that is formed in a side wall 211 of the furnace main body 21 and guides the gas to the gas analyzer 3, and a filter 23 that is provided so as to extend around the inner circumference of the side wall 211 inside the furnace main body 21.

Note that the filter 23 of the present embodiment is provided slightly apart from an intake port 221 of the gas outflow path 22 in the direction of the pipe axis of the furnace main body 21, and the gas generated as a result of the sample X being combusted inside the crucible 1 flows into the gas outflow path 22 via this filter 23.

The gas analyzer 3 analyzes the gas that is guided into the gas analyzer 3 through the gas outflow path 22, and thereby determines the content of each component contained in the sample X. In the present embodiment, the gas analyzer 3 performs this analysis by employing, for example, a non-dispersive infrared absorption method (NDIR method). Specifically, this gas analyzer 3 has a non-dispersive infrared detector (not shown) and determines the content of carbon (C) and sulfur (S) and the like contained in the sample X by detecting $CO_2$, CO, $SO_2$, and the like that are contained in the gas.

The oxygen supply mechanism 4 supplies oxygen to the interior of the heating furnace 2. Specifically, the oxygen supply mechanism 4 is equipped with a flow path forming component 41 in which a supply flow path L that supplies oxygen to the interior of the heating furnace 2 is formed, and with an oxygen cylinder which serves as an oxygen supply source 42 that is used to feed oxygen to the supply flow path L.

The flow path forming component 41 is a substantially block-shaped component, and is mounted such that it penetrates a top surface 212 of the heating furnace 2 in order to supply the oxygen flowing along the supply flow path L to the interior of the heating furnace 2. Furthermore, a transmission window 411 that transmits laser light is formed in the flow path forming component 41 of the present embodiment, and this transmission window 411 is in the form of a transparent, flat plate in the present embodiment.

The supply flow path L has a rectilinear first flow path L1 and a, for example, rectilinear second flow path L2. One end of the first flow path L1 opens in the direction of the sample X inside the crucible 1, while the transmission window 411 is formed in the other end of the first flow path L1. One end of the second flow path L2 connects to the other end of the first flow path L1, while an inlet port 41b through which oxygen is introduced from the oxygen supply source 42 is formed in the other end of the second flow path L2. By employing this structure, the transmission window 411 is formed on the opposite side from an aperture 41a in the first flow path L1, and the transmission window 411, the aperture 41a, and the sample X inside the crucible 1 are positioned on a straight line.

In the present embodiment, the second flow path L2 is formed perpendicularly to the first flow path L1. Oxygen supplied from the oxygen supply source 42 firstly passes through this second flow path L2 before flowing through the first flow path L1, and is then blown directly onto the sample X via the aperture 41a in the first flow path L1.

The above-described flow path forming component 41 is formed such that it is able to be moved by a drive unit (not shown) in a direction that is parallel to the flow path direction of the first flow path L1. As a result, it is possible to adjust the height of the aperture 41a of the first flow path L1 inside the heating furnace 2.

Note that a cleaning body such as a brush or the like (not shown) is provided on an outer side surface of the flow path forming component 41. Inner surfaces of the filter 23 and the heating furnace 2 can be cleaned by this cleaning body as a result of the flow path forming component 41 being moved by the drive unit.

The induction heating mechanism 5 is an induced current generating mechanism that generates an induced current in the sample X held in the crucible 1 by means of high-frequency induction heating. Specifically, the induction heating mechanism 5 is equipped with a coil 51, and a power supply 52 that applies high-frequency AC voltage to the coil 51. In the present embodiment, the coil 51 is provided around the outer circumference of the furnace main body 21, and the height of the placement stand 8 is set such that the crucible 1 is positioned on the inside of the coil 51 when the high-frequency AC voltage is being applied to the coil 51. When the high-frequency AC voltage is being applied to the coil 51, conductive heat-generating elements contained in the crucible 1 are made to generate heat by the high-frequency induction heating so that the sample X inside the crucible 1 is heated.

The laser heating mechanism 6 is a laser irradiation mechanism that irradiates laser light onto the sample X. In the present embodiment, the laser heating mechanism 6 is equipped with a laser light source 61 that emits laser light. The laser light source 61 of the present embodiment is located above the furnace main body 21, and emits laser light perpendicularly towards the transmission window 411 of the above-described flow path forming component 41. Here, as is described above, because the transmission window 411, the aperture 41a and the sample X inside the crucible 1 are placed on a straight line, an optical path B of the laser light transmitted through the transmission window 411 is formed inside the supply flow path L and parallel with the flow direction of the supply flow path L. Specifically, laser light that has passed through the transmission window 411 is transmitted in the flow direction along the first flow path L1. This laser light then travels from the aperture 41a through the interior of the heating furnace 2 towards the sample X, and is irradiated directly onto the sample X.

Note that, in the present embodiment, a semiconductor laser that provides an output of between 45 W and 200 W is used for the laser light source 61.

Figure 2:
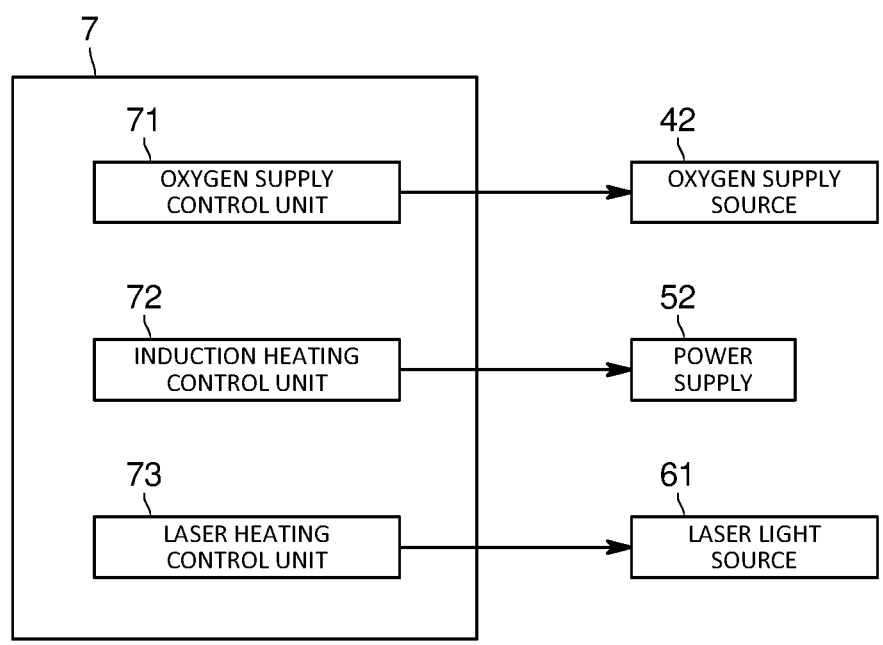
FIG. 2 is a functional block diagram showing functions of a control unit of the present embodiment.

In physical terms the control unit 7 is an electrical circuit formed by, for example, a CPU, internal memory, and an AD converter and the like. In functional terms, as is shown in FIG. 2, as a result of the CPU and peripheral devices working together in accordance with a program that is stored in the memory, the control unit 7 functions as an oxygen supply control unit 71, an induction heating control unit 72, and a laser heating control unit 73.

The oxygen supply control unit 71 adjusts the pressure or the flow rate of the oxygen that is supplied from the oxygen supply source 42 to the interior of the heating furnace 2 via the supply flow path L by transmitting a signal to the oxygen supply source 42.

The induction heating control unit 72 adjusts the output of the high-frequency AC voltage applied by the power supply 52 to the coil 51 by transmitting a signal to the power supply 52.

The laser heating control unit 73 adjusts the output of the laser light emitted by the laser light source 61 by transmitting a signal to the laser light source 61.

In the present embodiment, the induction heating control unit 72 and the laser heating control unit 73 control the induction heating mechanism 5 and the laser heating mechanism 6 such that the respective heating mechanisms 5 and 6 act simultaneously to heat the sample X. In other words, they perform control such that a state in which the induction heating mechanism 5 supplies an induced current to the sample X and a state in which the laser heating mechanism 6 irradiates laser light onto the sample X are generated simultaneously. More specifically, the induction heating control unit 72 and the laser heating control unit 73 control the respective heating mechanisms 5 and 6 such that a state in which the sample X is heated simultaneously by the induction heating mechanism 5 and the laser heating mechanism 6 continues for a predetermined length of time.

Even more specifically, the induction heating control unit 72 transmits a signal to the power supply 52 at the same time as the laser heating control unit 73 transmits a signal to the laser light source 61. In addition, the induction heating control unit 72 controls the power supply 52 such that the high-frequency AC voltage is supplied continuously from the power supply 52 to the coil 51, for example, for 30 seconds, while the laser heating control unit 73 controls the controls the laser light source 61 such that the laser light is irradiated continuously from the laser light source 61 onto the sample X, for example, for 30 seconds.

As a result, the sample X is heated simultaneously by the induction heating mechanism 5 and the laser heating mechanism 6 for a period of 30 seconds. Note that the length of this heating period is not limited to 30 seconds and can be set to a desired time depending on the sample X.

According to the elemental analysis device 100 of the present embodiment having the above-described structure, because the induction heating mechanism 5 and the laser heating mechanism 6 simultaneously heat the sample X, it is possible to efficiently heat the sample X and thereby accelerate the combustion thereof. Moreover, it is not necessary for a combustion improver to be used. Because there is no need to use a combustion improver, no dust that is created by the combustion improver is generated. Accordingly, there is no need for a dust suction mechanism to be provided, and no measurement errors that are caused by gas adhering to the dust are generated.

Moreover, because the optical path B of the laser light transmitted through the transmission window 411 is formed inside the first flow path L1, the existing supply flow path L is able to also function as the optical path B of the laser light. Accordingly, there is no need to create a complicated structure to irradiate laser light onto the sample X.

Furthermore, because the transmission window 411 is formed on the first flow path L1 on the opposite side from the aperture 41*a*, and oxygen is supplied through this aperture 41*a* into the interior of the heating furnace 2, it is possible to prevent soot and the like that is inside the heating furnace 2 from flowing back along the first flow path L1 and becoming adhered to the transmission window 411.

In addition, because the gas generated inside the heating furnace 2 flows through the gas outflow path 22 via the filter 23, it is possible to prevent dust such as soot and the like from entering into the gas analyzer 3.

Moreover, because a drive unit (not shown) is able to adjust the height of the aperture 41*a* of the first flow path L1 inside the heating furnace 2 by moving the flow path forming component 41, it is possible to place the sample X in the optimum state of combustion by controlling the speed at which oxygen is supplied to the sample X.

Note that the present invention is not limited to the above-described embodiment.

For example, in the above-described embodiment, the induction heating mechanism and the laser heating mechanism transmit signals simultaneously to the power supply and the laser light source respectively, however, it is not absolutely essential for these signals to be transmitted simultaneously, and it is also possible for the signals to be transmitted after predetermined time intervals. Namely, provided that there is a period in which the heating by the induction heating mechanism and the heating by the laser heating mechanism are performed simultaneously, then it is acceptable for the start times of the heatings performed by the respective mechanisms to be mutually different, and for the end times of these heatings to also be mutually different.

Figure 3:
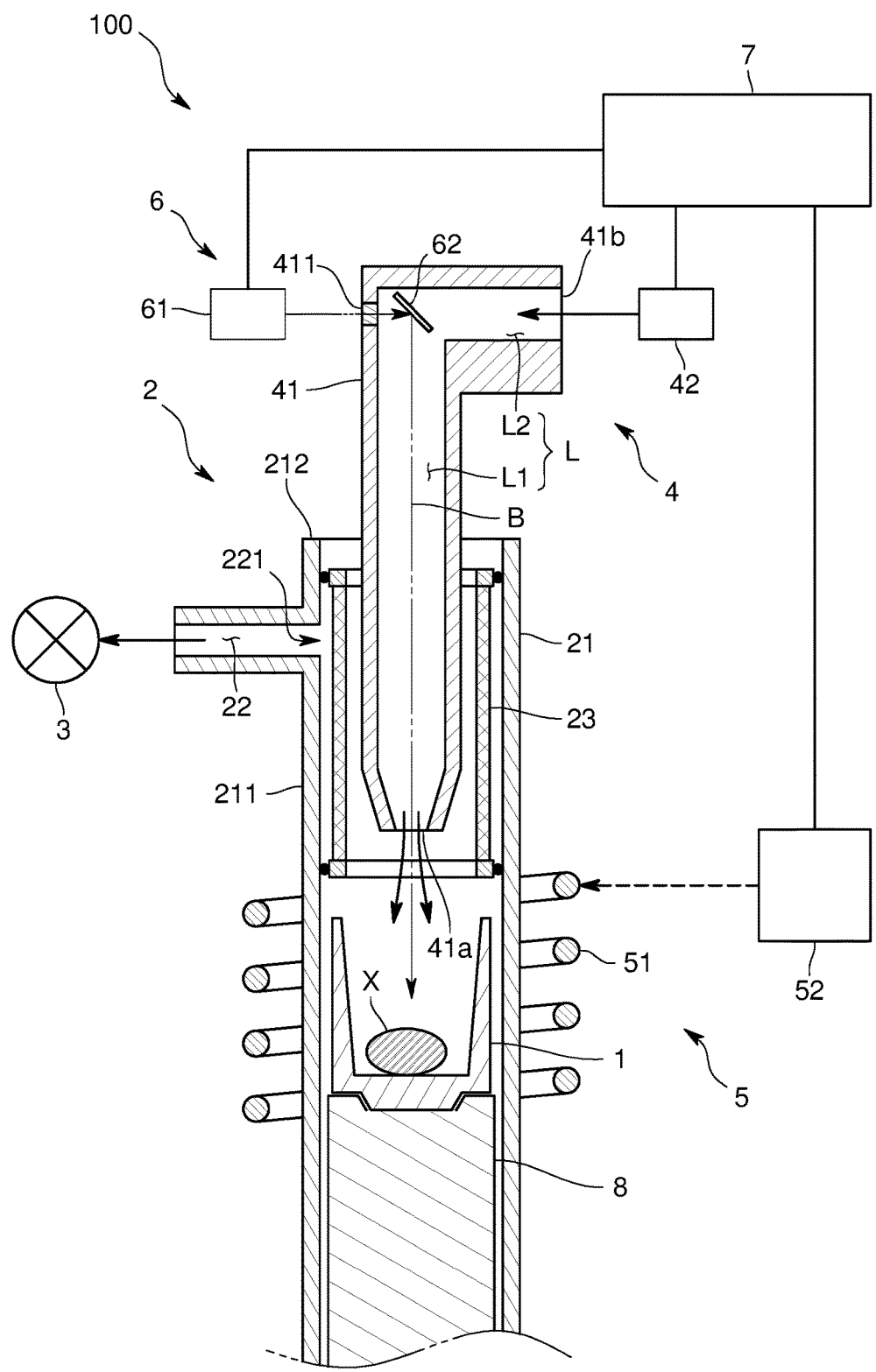
FIG. 3 schematically shows the structure of an elemental analyzer according to a variant embodiment.

Moreover, in the above-described embodiment, the transmission window is formed on the opposite side from the aperture on the first flow path, however, as is shown in FIG. 3, it is also possible, for example, for the transmission window 411 to be formed on the opposite side from the oxygen supply source 42 on the second flow path L2, and for the laser light that has passed through the transmission window 411, for example, to be reflected by an optical component such as a reflection mirror 62 or the like such that it is irradiated onto the sample X.

Moreover, in the above-described embodiment, the coil is provided around the outer circumference of the furnace main body, however, it is also possible for the coil to be provided, for example in the bottom portion of the crucible, or on the top surface of the placement stand.

Moreover, it is also possible to introduce a carrier gas into the interior of the heating furnace from underneath the heating furnace in order to enable the gas that is combusted inside the crucible to flow efficiently along the gas outflow path. A gas that contains oxygen may be used for this type of carrier gas.

Furthermore, in the above-described embodiment, only a sample is held inside the crucible, however, it is also possible to place a combustion improver inside the crucible in addition to the sample and to thereby further accelerate the combustion of the sample.

Furthermore, the supply flow path L of the above-described embodiment is used to supply oxygen to the interior of the sample holding portion, however, it is also possible to employ a structure in which the supply flow path L supplies another gas (which may be an oxygen-containing gas) to the interior of the sample holding portion, and the laser light is irradiated onto the sample after being transmitted through this supply flow path L. Alternatively, it is also possible to employ a structure in which, in addition to the supply flow path L that supplies oxygen to the interior of the sample holding portion, there is provided a second supply flow path L that supplies another gas (which may be an oxygen-containing gas) to the interior of the sample holding portion, and the laser light is irradiated onto the sample after being transmitted through this second supply flow path.

It should also be noted that the present invention is not limited to the above-described embodiment, and various modifications and the like may be made thereto insofar as they do not depart from the spirit or scope of the present invention.

INDUSTRIAL APPLICABILITY

According to the present invention, it is possible to efficiently heat and combust a sample without using a combustion improver, while guaranteeing sufficient ease of operability during calibration.

What is claimed is:

1. An analysis device that heats a sample inside a sample holding portion, and analyzes the gas that is thereby generated,
   wherein the analysis device comprising:
   an induced current generating mechanism that generates by electromagnetic induction an induced current in the sample; and
   a laser irradiation mechanism that irradiates laser light onto the sample, and
   the induced current generating mechanism and the laser irradiation mechanism are made to act simultaneously on the sample.

2. The analysis device according to claim 1, further comprising a flow path forming component in which a supply flow path that supplies oxygen into the sample holding portion is formed, and
   a transmission window that allows to transmit laser light is formed in the flow path forming component, and an optical path of the laser light that has been transmitted through the transmission window is formed inside the supply flow path along with the flow path direction of the supply flow path.

3. The analysis device according to claim 2, wherein the supply flow path has a rectilinear flow path having one end that opens in the direction of the sample, and having the transmission window formed in the other end thereof.

4. An analysis method in which a sample is heated inside a sample holding portion, and the resulting gas that is thereby generated is analyzed, wherein
   the sample is heated by an induced current generating mechanism, which generates an induced current in the sample by electromagnetic induction, and by a laser irradiation mechanism, which irradiates laser light onto the sample, acting on the sample simultaneously.

* * * * *